United States Patent [19]

Whitefield

[11] Patent Number: 5,088,145
[45] Date of Patent: Feb. 18, 1992

[54] ELECTRICALLY POWERED TOOTHBRUSH

[76] Inventor: Robert O. Whitefield, 19909 - 163rd Ave. NE., Woodinville, Wash. 98072

[21] Appl. No.: 498,895

[22] Filed: Mar. 26, 1990

[51] Int. Cl.⁵ ............................................. A61C 17/16
[52] U.S. Cl. .................................... 15/22.1; 15/22.2; 15/167.1; 15/167.2
[58] Field of Search ................ 15/22.1, 22.2, 167.1, 15/167.2; 335/128

[56] References Cited

U.S. PATENT DOCUMENTS

| | | | |
|---|---|---|---|
| 2,583,886 | 1/1952 | Schlegel | 15/167.1 X |
| 2,598,275 | 5/1952 | Lakin | 15/167.1 X |
| 2,655,676 | 10/1953 | Grover | 15/167.1 X |
| 2,657,321 | 10/1953 | Smithson, Jr. | 15/167.1 X |
| 2,682,066 | 6/1954 | Keely | 15/167.2 X |
| 2,882,544 | 4/1959 | Hadidian | 15/167.1 |
| 3,082,457 | 3/1963 | Lucibello et al. | 15/167.1 |
| 3,512,201 | 5/1970 | Taylor | 15/22.1 X |
| 3,677,264 | 7/1972 | Brockman | 15/167.2 X |
| 4,156,620 | 5/1979 | Clemens | 15/22.1 X |
| 4,274,173 | 6/1981 | Cohen | 15/167.1 X |
| 4,344,202 | 8/1982 | Hayat | 15/22.1 X |
| 4,346,492 | 8/1982 | Solow | 15/22.1 |
| 4,397,055 | 8/1983 | Cuchiara | 15/22.1 |
| 4,471,504 | 9/1984 | Andersson | 15/22.1 |
| 4,545,087 | 10/1985 | Nahum | 15/22.1 |
| 4,603,448 | 8/1986 | Middleton et al. | 15/22.1 |
| 4,827,550 | 5/1989 | Graham et al. | 15/22.1 |

FOREIGN PATENT DOCUMENTS

| | | | |
|---|---|---|---|
| 357863A | 3/1990 | European Pat. Off. | 15/22.1 |
| 2400787 | 7/1975 | Fed. Rep. of Germany | 15/22.1 |
| 2736286 | 12/1978 | Fed. Rep. of Germany | 15/22.1 |
| 3334841 | 4/1985 | Fed. Rep. of Germany | 15/22.1 |
| 3544256A | 6/1987 | Fed. Rep. of Germany | 15/22.1 |

Primary Examiner—William A. Cuchlinski, Jr.
Assistant Examiner—James Folker
Attorney, Agent, or Firm—H. Albert Richardson

[57] ABSTRACT

A portable electrically powered toothbrush which includes a brush head having at least one tuft holding assembly mounted for rotation about its central axis. Pulsating direct current is supplied through control circuitry to a DC motor in the brush handles by a pair of rechargeable batteries also mounted in the handle. Power from the motor is transmitted through a reduction gear and belt drive assembly to the tuft holding assembly, resulting in a unidirectional intermittent rotation of the assembly about its axis and a simultaneous reciprocation of the assembly along that axis. Alternately, continuous power may be supplied to the motor, resulting in a unidirectional continuous rotation and reciprocation of the tuft holding assembly.

19 Claims, 6 Drawing Sheets

ELECTRICALLY POWERED TOOTHBRUSH

BACKGROUND OF THE INVENTION

This invention generally relates to oral hygiene devices and more particularly to a portable electrically powered toothbrush in which a unique combination of rotational and reciprocating motion is imparted to the tufts or bristles.

In order to promote and facilitate dental hygiene significant effort has been made in recent decades to develop powered tooth cleaning devices which improve upon the conventional hand held toothbrush. Many of these devices have been designed in view of new and improved dental hygiene techniques and brushing methods which have from time to time been suggested by researchers in the field.

These powered devices generally fall into one of two categories. The first category utilizes brush heads which closely resemble the heads of conventional unpowered toothbrushes and have tufts and bristles mounted in them. In operation these devices move the brush heads with respect to the handle in a variety of rotary, arcuate, reciprocating or orbital paths. The second category has brush heads which remain stationary with respect to the brush handle during operation and in which individual tufts are rotated or oscillated. Broadly speaking, the present invention falls into the second category of such devices.

It has long been recognized that the use of tufts having a circular motion is a highly effective cleaning technique and offers many advantages over the non-powered brush. The circular action not only cleans and brushes the surfaces of teeth but aids in the removal of stains from the teeth and has a therapeutic effect for gum tissue. It has been argued, however, that if the tufts are moved in a continuous unidirectional circular motion, the tips of the bristles will merely pass over most of the crevices in the tooth surfaces and between the teeth and the gingiva. As a result such brushes will fail to remove much of the dental plaque from tooth surfaces.

Accordingly, it is a principal object of this invention to provide for an improved powered toothbrush in which each individual tuft is rotated in an intermittent unidirectional manner about its axis and simultaneously reciprocated along that axis to provide better penetration by the tips of the bristles into tooth crevices and between the teeth and gingiva and thereby more effectively remove dental plaque from tooth surfaces and gingival tissues.

It is another object of this invention to provide for an improved powered toothbrush in which a greater amount of torque is delivered to the rotating tufts in operation than found in previously known devices.

It is a further object of this invention to provide for a powered toothbrush in which the brush head can be quickly and conveniently removed from the handle, thus permitting each user to employ his or her personal brush head when using the device and permitting the installation of various attachments such as tooth polishing devices to the handle.

It is a further object of this invention to provide for an improved powered toothbrush which is made fully portable by the use of rechargeable batteries as a source of power, which is relatively light in weight, and which is convenient to use.

SUMMARY OF THE INVENTION

This invention can be broadly summarized as providing for a powered device for cleaning teeth which includes a brush head having at least one tuft holding assembly mounted for rotation about its central axis. It also includes means for rotating the tuft holding assembly in a unidirectional intermittent manner about its axis and means for reciprocating the assembly in a direction along the axis simultaneously with the rotation.

In accordance with a more detailed aspect of the invention the device includes a plurality of tuft holding assemblies arranged in staggered rows in the brush head, each mounted for rotation about its central axis. It also includes means for rotating the tufts in a unidirectional, intermittent manner, control means for periodically interrupting such rotation and means for reciprocating each of the tuft holding assemblies along its central axis simultaneously with the rotation.

DESCRIPTION OF THE PREFERRED EMBODIMENT

Figure 1:
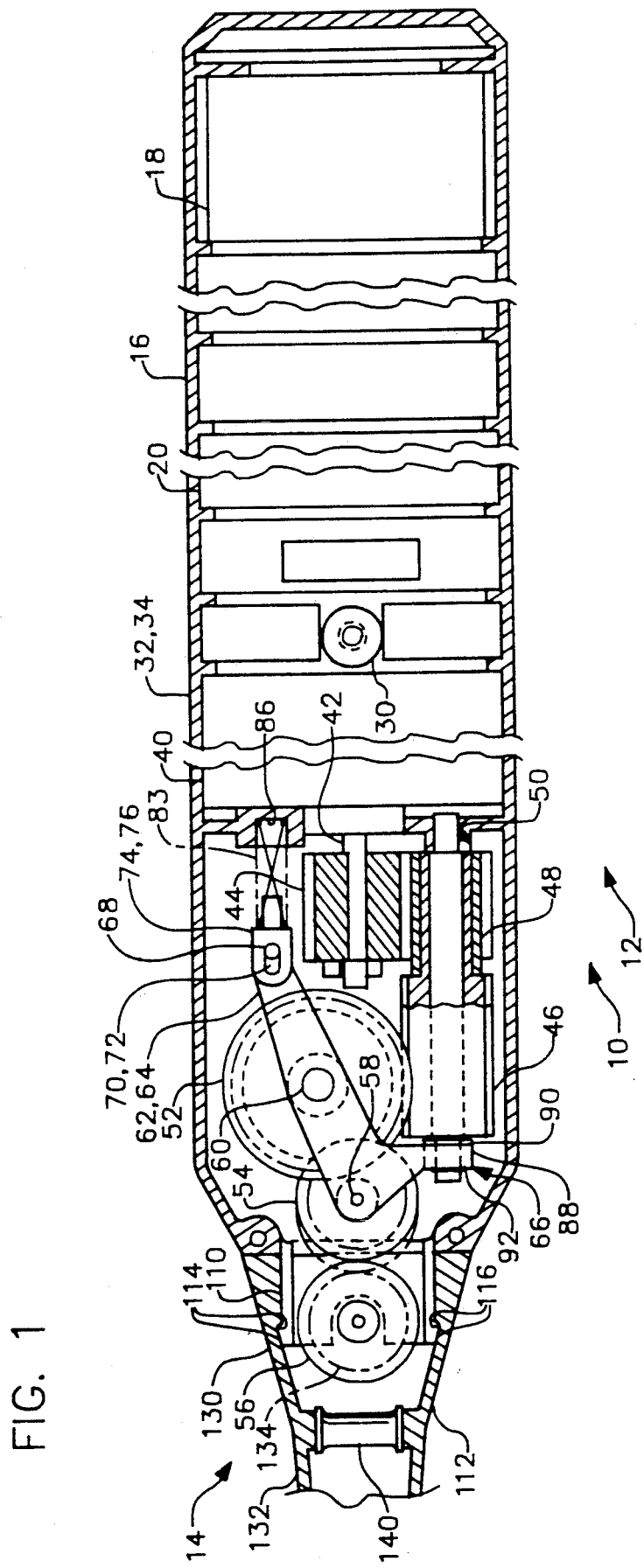
FIG. 1 is a bottom view in section of the handle portion of the present invention.
Figure 2:
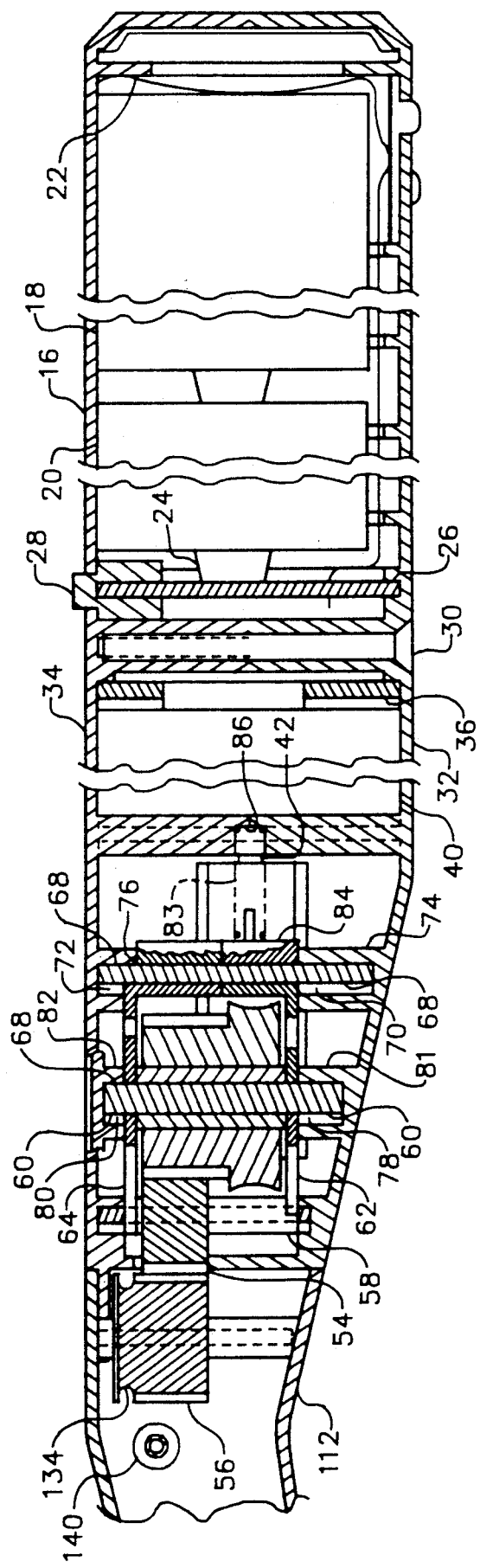
FIG. 2 is a side view of the handle portion, also in section.

The novel features believed to be characteristic of this invention are set forth in the appended claims. The invention itself, however, may be best understood and its various objects and advantages best appreciated by reference to the detailed description below in connection with the accompanying drawings.

In FIGS. 1 through 6 of those drawings an electrically powered toothbrush constructed in accordance with the teachings of the present invention is illustrated and generally designated by the number 10. The device includes a handle section generally designated by the number 12 and shown in detail in FIGS. 1 and 2. It also includes a detachable brush head generally designated by the number 14 and shown in FIGS. 3 and 4.

The handle section includes a case 16 which houses batteries, an electric motor, electronic circuitry and controls, and a gear drive assembly. Preferably, each battery 18 and 20 is a nominal 2.5 volt size D NICd rechargeable cell. The batteries are installed in series and the base or negative terminal of cell 18 is in contact with ground strip 22. Both the ground strip and positive terminal 24 of cell 20 are in contact with circuit board 26 upon which slideable control switch 28 is mounted. Preferably the control switch has an "off" position, and first and second operation positions. Access to the batteries and other components enclosed in the handle may be obtained by removing screw 30 which joins halves 32 and 34 of the handle.

Figure 5:
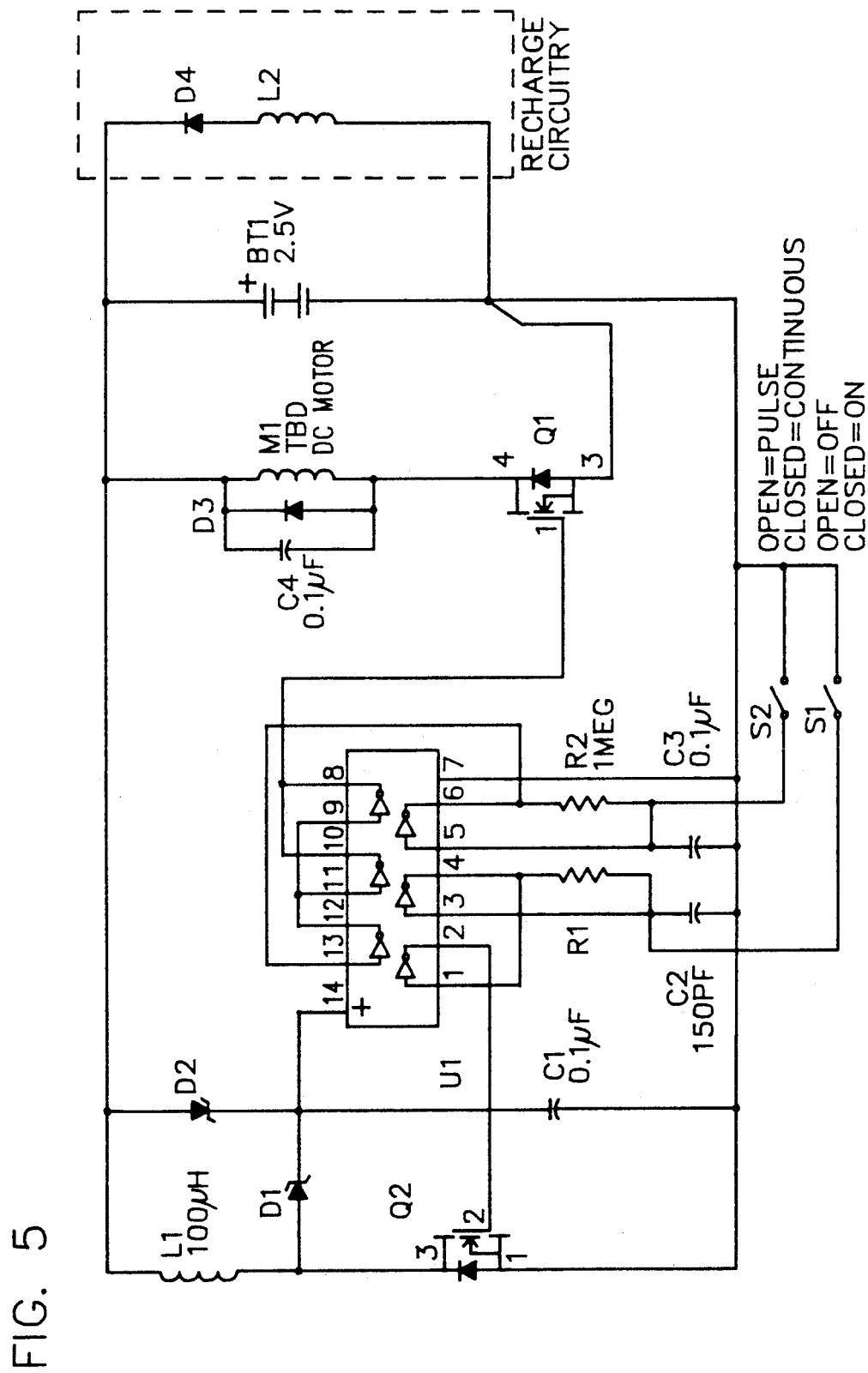
FIG. 5 is an electrical circuit diagram for the present invention.

The remainder of the electronic components of the invention are mounted on circuit board 36, which is electrically interconnected with board 26 as shown in the electrical circuit diagram of FIG. 5. Referring to FIG. 5 it can be seen that switching charge pump L1/D1/Q2/U1/R1/C2 effectively increases the voltage available from the batteries to approximately 12V for use with the pulsing circuit. The charge pump switches at about 3900 kHz, which is produced by RC oscillator R1/C2/U1/(3-4). Q2 is a low-threshold MOSFET suitable for low initial turn-on voltage. Zener diode D2 shunts excess current back to the battery, clamping the internal supply to 10V above battery voltage. Switch 28, which combines S1 and S2, turns the supply off and on. Pulse/Continuous Controller R2/C3/U1/Q1 is operated by opening or closing switch S2. Closing S2 disables pulse oscillator R2/C3/U1(5-6), setting power switch Q1 to "on". Conversely, opening S2 allows the pulse oscillator to turn Q1 on and off at a rate determined by the product of R2 and C3. The pulse duty cycle is approximately 50% and the total drain on the battery (over motor current) when the brush is operating is about 10 milliamperes. When it is off, the battery drain is insignificant. Recharging of the batteries is accomplished through means well known to those of ordinary skill in the art and is not described in detail. Those means include a transformer coil mounted in a base/stand, not shown.

One innovative aspect of the above described electronic circuitry is that control switches S1/S2 carry almost no current. By comparison, the control switches of other currently available electric toothbrushes would be required to handle over ten amperes if the motor stalled or became jammed. Accordingly, relatively small and light-duty switch contacts will suffice for use in the present invention. Also, the electronics produce an efficient pulsating action and have a long projected life. Further, the design avoids the use of mechanical switches which would be prone to wear out. If desired, the circuitry could be modified to permit adjustment of the pulse rate by the user.

Power from the circuitry is provided to DC motor 40 which is positioned in case 16 just forward of circuit board 34. Mounted on motor output shaft 42 is pinion gear 44 which drives worm 46 through spur gear pinion 48. As shown in FIG. 1, worm 46 and spur gear pinion 48 are mounted for rotation on common shaft 50. Power from the worm is transferred successively to worm gear 52, spur gear 54 and finally to spur gear 56, which is mounted for rotation in detachable brush head 14.

In order to facilitate positive engagement of spur gears 54 and 56 when the brush head is attached to the handle, spur gear 54 has been mounted to permit a small degree of translation along the center line of housing 16 and is spring biased toward gear 56. As shown in the drawings, gears 52 and 54 are mounted for rotation on shafts 58 and 60, respectively, which in turn are mounted to parallel arms 62 and 64 of yoke 66. The yoke is partially supported in the housing by pin 68 which passes through arms 62 and 64 and is mounted for translation in slots 70 and 72 formed in housing protrusions 74 and 76, respectively. The yoke is also supported by shaft 60 which extends into slotted recesses 78 and 80 in housing protrusions 81 and 82, respectively. Spring 83 (shown schematically) extends between surface 84 of the yoke and spring pocket 86 in the housing and biases the yoke to the left. Lower section 88 of the yoke houses nylon bushing 90 which supports left hand end of shaft 50. The shaft is retained in position by worm 46 and retainer 92 which is attached to the shaft.

Brush head 14 is removably attached to handle 12 by the interconnection of neck 110 of the handle and throat 112 of the head. Annular ridge 114 of the neck cooperates with annular recess 116 of the throat to retain the brush head securely in position. The brush head and the handle can be easily separated by grasping the handle in one hand and the head in the other and pulling them apart. One advantage of this design is that when the handle and head are separated, gears 54 and 56 are recessed in neck 110 and throat 112, respectively, and are thereby protected from damage if either section is accidently dropped.

Figure 3:
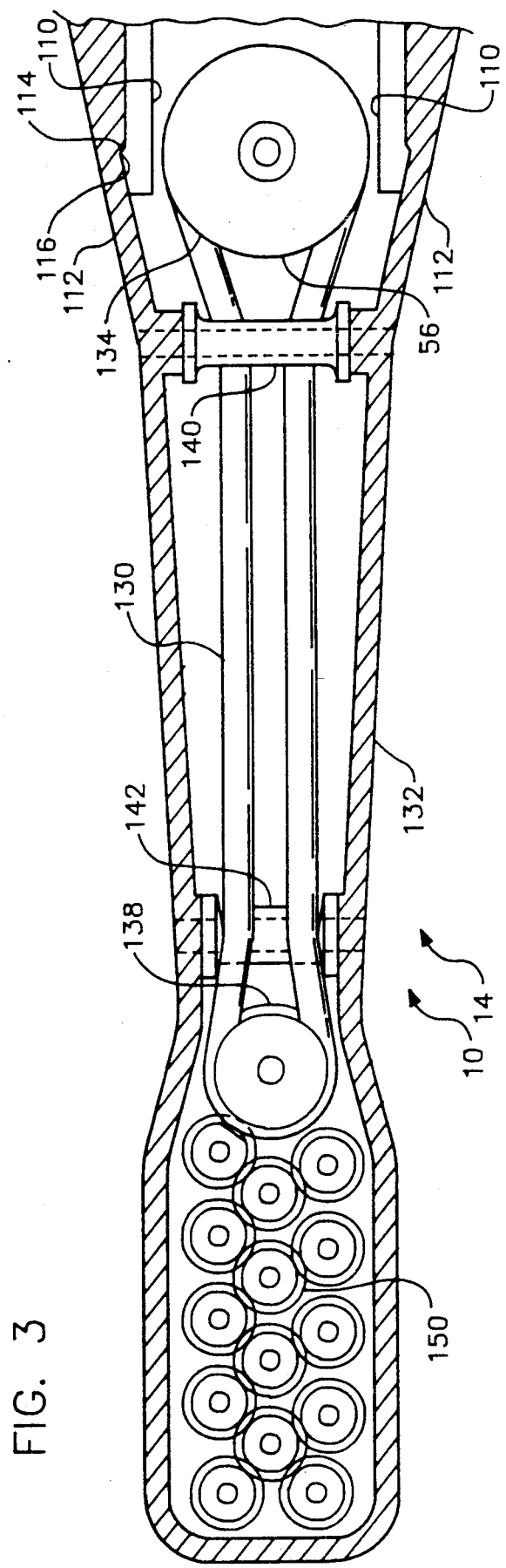
FIG. 3 is a bottom view in section of the head portion of the present invention.
Figure 4:
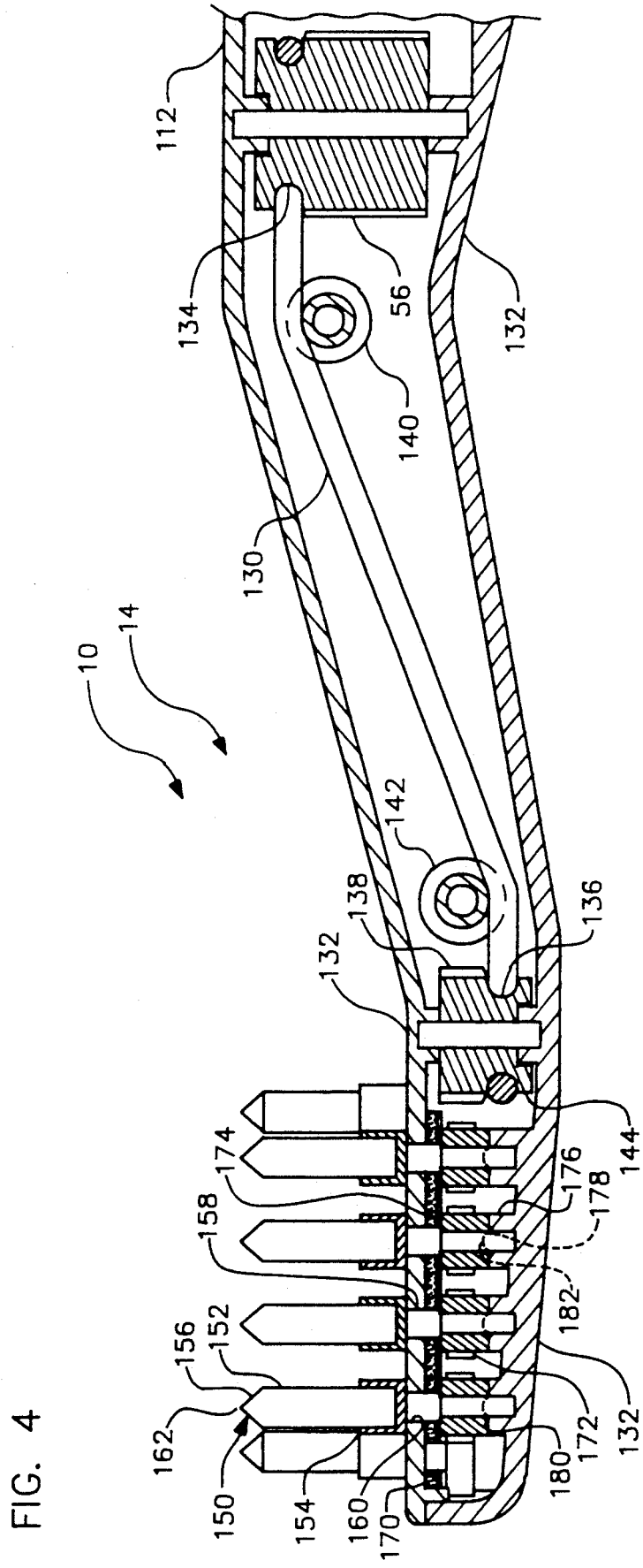
FIG. 4 is a side view of the handle portion, also in section.

Referring to FIG. 3, power from spur gear 56 is transferred along the handle by endless belt 130 which extends between pulley 134 formed atop spur gear 56 and pulley 136, which is formed in spur gear 138. Preferably, the belt is circular in cross section and formed of polyurethane. In order to accommodate the internal contours of head housing 132 the belt is caused to pass over guide rollers 140 and 142, each of which is mounted for rotation in housing 132.

Figure 6:
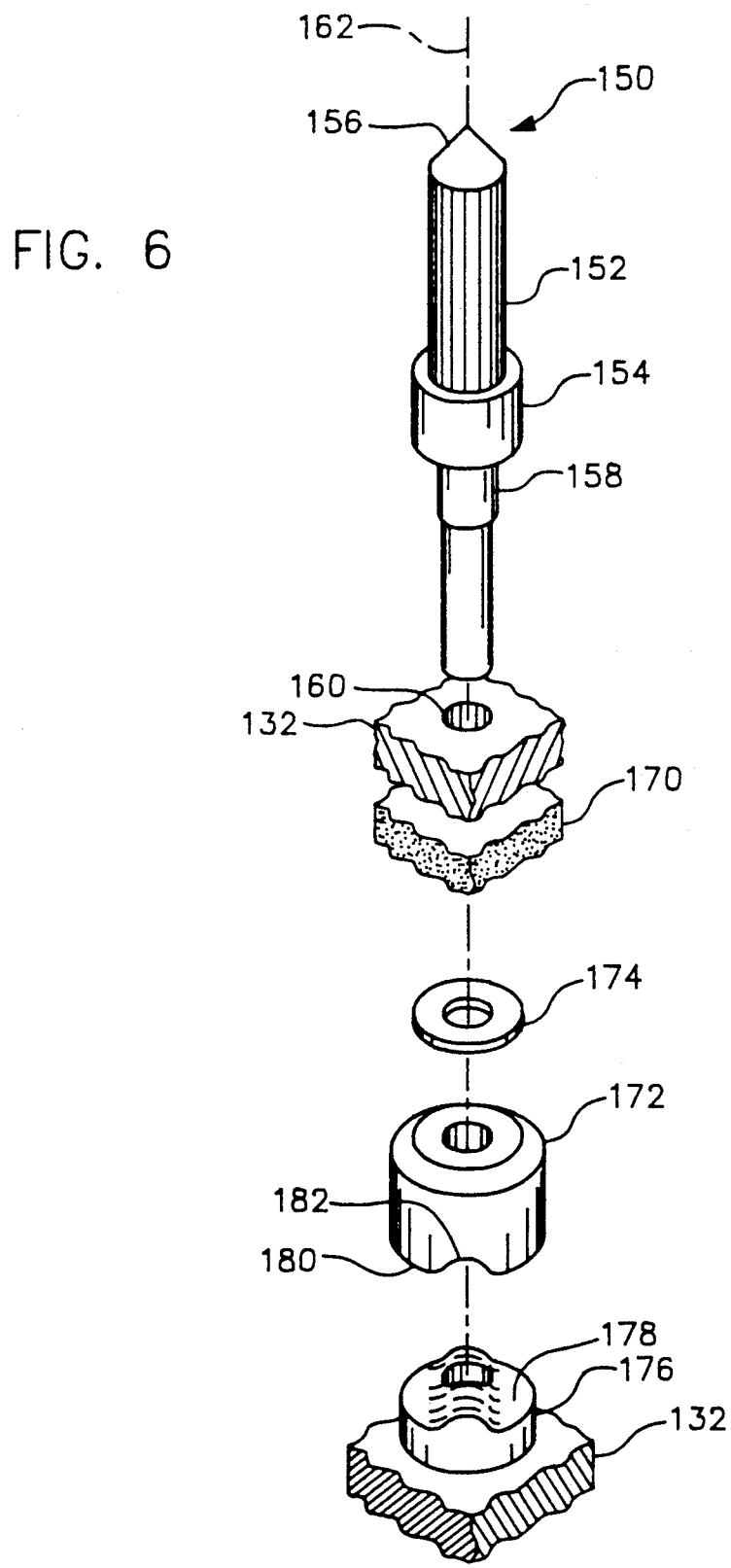
FIG. 6 is an exploded perspective view of a typical tuft holding assembly of the present invention.

A plurality of tuft holding assemblies, of which assembly 150 is typical, are mounted for rotation in the brush head. FIG. 6 is an exploded view diagram showing tuft holding assembly 150 and a portion of the brush head. The assembly includes a plurality of bristles 152, preferably made of nylon, which are securely mounted in cylindrical base 154 and trimmed to form conical tip 156. Shaft 158, which is attached to base 154, is adapted to closely fit into circular hole 160. The clearance between the shaft and the wall of the hole is adequate to permit the shaft to rotate freely about its axis 162 but small enough to permit water to form a meniscus therebetween. Accordingly, little if any water will be permitted to pass into the housing through the tuft holding assembly mounting holes.

Positioned immediately inside the housing is spring pad 170 which is preferably formed from closed cell neoprene foam. An array of holes is formed in the pad corresponding to the axes of rotation of the tuft holding assemblies, permitting the assembly drive shafts, such as shaft 158, to pass through. The purpose of the pad is to bias shaft 158 in a downward direction and to provide a second barrier against the passage of liquid further into the housing. Fixed to the lower portion of each drive shaft is spur gear 172 which engages gear 138 and is spaced from spring pad 170 by a shim washer 174. Cylindrical protrusion 176 extends upward from the lower portion of housing 132 and its upper surface is formed to provide a convex face cam 178. Lower surface 180 of spur gear 172, which functions as a cam follower, is adapted to ride on face cam 178 as it rotates. Each of the remaining assemblies includes a spur gear similar to gear 172 by which it is interconnected to gear 138. The gearing arrangement shown results in rotation of each assembly in a given row in the same sense and rotation of assemblies in adjoining rows in the opposite sense.

In order to operate the invention, the user first moves switch 28 from the off position to the first operating position, thereby placing S1 in a closed position and leaving S2 in an open position. In this condition a pulsating current is supplied to motor 40, resulting in an intermittent unidirectional motion of output shaft 42, that motion is subsequently transmitted to worm 46, the worm and spur gear assembly, belt 130, spur gear 138 and each of the spur gears such as gear 172 to each of the tuft holding assemblies. Referring again to FIG. 6, it can be seen that as assembly 150 is rotated, lower surface 180 of spur gear 172 will ride on face cam 178, causing shaft 158 to reciprocate along axis 162. Due to the biasing action of spring pad 170, surface 180 will tend to stay in contact with cam face 178 as it rotates. Accordingly, placing switch 28 in the first operating position will result in an intermittent, unidirectional rotation of the holding assembly about its axis and a simultaneous reciprocation along that axis.

Movement of switch 28 into the second operating position will result in a continued closure of S1 and a movement of S2 into the closed position. In that condition, as previously discussed, the pulse oscillator is disabled and a continuous current will be transmitted to the motor resulting in a continuous rotation of the tuft holding assemblies and a simultaneous reciprocation of them about their individual axes.

Thus, it can be seen that the present invention provides for an improved electrically powered toothbrush which incorporates many novel features and offers significant advantages over the prior art. Although only one embodiment of this invention has been illustrated and described, it is to be understood that obvious modifications can be made in it without departing from the true scope and spirit of the invention. For example, it would be obvious to modify the drive system by substituting a drive shaft and pinion gear arrangement for the drive belt or the spur gear assembly, or both. Also, it would be obvious to substitute other arrangements of tuft holding assemblies in the head, other sources of power, other means to provide an intermittent power source, or other means to reciprocate the tuft holding assemblies.

I claim:

1. A device for cleaning teeth comprising:
   a brush head;
   at least one tuft holding assembly mounted in the head for rotation about its central axis;
   means for automatically rotating the assembly in both an intermittent and a unidirectional manner about the central axis; and,
   means for reciprocating the holding assembly with respect to the brush head along the central axis simultaneously with the rotation.

2. The device of claim 1 wherein the means for rotating includes electric power means and gearing means connecting the power means to the holding assembly.

3. The device of claim 2 wherein the gearing means includes a first gear assembly connected to the power means, a second gear assembly connected to the holding assembly and an endless belt connecting the first and second gear assemblies.

4. The device of claim 3 wherein the first gear assembly includes a worm driveably connected to the power means, a worm gear connected to the worm, and at least one spur gear connected to the worm gear.

5. The device of claim 1 further including a handle and wherein the head is removably attached to the handle.

6. The device of claim 5 wherein a first portion of the means for rotating is disposed in the handle and a second portion of the means for rotation is disposed within the head, the first portion being adapted to engage the second portion upon attachment of the head to the handle, and wherein one of the portions is displaceably mounted and biased toward a position of engagement with the other.

7. The device of claim 5 wherein the first portion includes a yoke displaceably mounted within the handle, at least one gear rotatably mounted on the yoke and adapted to engage the second portion and means for biasing the yoke into engagement with the second portion.

8. The device of claim 6 wherein the handle includes a neck protectably enclosing the first portion and adapted to removably engage the head.

9. The device of claim 1 including a plurality of tuft holding assemblies and a plurality of gears, each connected to one of the holding assemblies and also connected to at least one other of the gears, power means, and means connecting at least one of the gears to the power means.

10. The device of claim 9 wherein the plurality of tuft holding assemblies are arranged in at least one row.

11. The device of claim 9 wherein the tuft holding assemblies are arranged in a plurality of rows and wherein all assemblies in a given row are adapted to rotate in a common sense.

12. The device of claim 11 wherein the holding assemblies in adjacent rows are adapted to rotate in the opposite sense.

13. The device of claim 1 wherein the means for rotating includes an electric motor and electronic control means for supplying a pulsating electric current to the motor.

14. A device for cleaning teeth comprising:
   a brush head;
   a plurality of tuft holding assemblies each mounted in the head for rotation about its central axis;
   a plurality of gears each connected to one of the holding assemblies and also connected to one of the other gears;
   means for rotating each holding assembly in an intermittent, unidirectional manner including an electric motor and electronic control means for supplying a pulsating electric current to the motor, and
   means for reciprocating each assembly along its central axis simultaneously with the rotation.

15. The device of claim 1 wherein the means for reciprocating includes a cam and a cam follower.

16. The device of claim 1 wherein the means for reciprocating includes a face cam connected to the holding assembly and a cam follower connected to the brush head.

17. The device of claim 15 further including means for biasing the cam and cam follower into engagement.

18. The device of claim 17 wherein the biasing means includes a compressible foam pad disposed within the brush head.

19. A device for cleaning teeth comprising:
   a brush head;
   a plurality of tuft holding assemblies each mounted in the head for rotation about its central axis;
   a plurality of gears each connected to one of the holding assemblies and also connected to one of the other gears;
   means for rotating each holding assembly in an intermittent, unidirectional manner including an electric motor and electronic control means for supplying a pulsating electric current to the motor; and,
   means for reciprocating each assembly along its central axis simultaneously with the rotation including a face cam connected to the holding assembly, a cam follower connected to the brush head, and means for biasing the cam and cam follower into engagement.

* * * * *